US009808653B2

(12) United States Patent
Newell

(10) Patent No.: US 9,808,653 B2
(45) Date of Patent: Nov. 7, 2017

(54) TREATMENT OF SUBARACHNOID HEMATOMA USING SONOTHROMBOLYSIS AND ASSOCIATED DEVICES, SYSTEMS AND METHODS

(71) Applicant: David W. Newell, Seattle, WA (US)

(72) Inventor: David W. Newell, Seattle, WA (US)

( * ) Notice: Subject to any disclaimer, the term of this patent is extended or adjusted under 35 U.S.C. 154(b) by 1077 days.

(21) Appl. No.: 13/902,644

(22) Filed: May 24, 2013

(65) Prior Publication Data

US 2013/0338544 A1 Dec. 19, 2013

Related U.S. Application Data

(60) Provisional application No. 61/659,269, filed on Jun. 13, 2012.

(51) Int. Cl.
*A61H 1/00* (2006.01)
*A61N 7/02* (2006.01)
(Continued)

(52) U.S. Cl.
CPC .......... *A61N 7/02* (2013.01); *A61B 17/22004* (2013.01); *A61B 90/10* (2016.02);
(Continued)

(58) Field of Classification Search
None
See application file for complete search history.

(56) References Cited

U.S. PATENT DOCUMENTS 6,471,683 B2 10/2002 Drasler et al.
6,733,450 B1 5/2004 Alexandrov et al.
(Continued)

FOREIGN PATENT DOCUMENTS

EP 1591073 A1 11/2005
JP 03222961 A 10/1991
(Continued)

OTHER PUBLICATIONS

Abdu, Emun, et al., "Minimally invasive treatment for intracerebral hemorrhage," *Neurosurg Focus*. Apr. 2012. (7 pgs).
(Continued)

*Primary Examiner* — Amanda Lauritzen Moher
*Assistant Examiner* — Shahdeep Mohammed
(74) *Attorney, Agent, or Firm* — Perkins Coie LLP

(57) ABSTRACT

Methods for treating a human patient having a subarachnoid hematoma, such as to prevent cerebral vasospasm or to reduce the severity of cerebral vasospasm in the patient, and associated devices, systems, and methods are disclosed herein. In a particular embodiment, a thrombolytic agent is introduced extravascularly into a subarachnoid region including the hematoma. A headset configured for hands-free delivery of transcranial ultrasound energy is connected to the patient and used to deliver ultrasound energy to the subarachnoid region to enhance the thrombolytic effect of the thrombolytic agent. The type and/or dosage of the thrombolytic agent can be selected based on the enhanced thrombolytic effect. For example, the enhanced thrombolytic effect can allow the therapeutically effective use of less aggressive thrombolytic agents and/or lower dosages of thrombolytic agents. In some cases, this can reduce the clinical probability of additional cerebral hemorrhage.

21 Claims, 7 Drawing Sheets

(51) Int. Cl.
  *A61N 7/00* (2006.01)
  *A61B 17/22* (2006.01)
  *A61B 90/10* (2016.01)
  *A61B 8/08* (2006.01)
  *A61B 8/06* (2006.01)

(52) U.S. Cl.
  CPC .................. *A61N 7/00* (2013.01); *A61B 8/06* (2013.01); *A61B 8/0808* (2013.01); *A61B 8/488* (2013.01); *A61N 2007/0021* (2013.01); *A61N 2007/0052* (2013.01); *A61N 2007/0078* (2013.01)

(56) References Cited

U.S. PATENT DOCUMENTS

| | | | |
|---|---|---|---|
| 2004/0209307 A1* | 10/2004 | Valkirs ................ | C12Q 1/6883 435/7.1 |
| 2005/0085748 A1 | 4/2005 | Culp et al. | |
| 2006/0058678 A1* | 3/2006 | Vitek .................. | A61B 8/4281 600/459 |
| 2006/0142732 A1* | 6/2006 | Karmarkar ......... | A61M 25/0138 604/508 |
| 2008/0089912 A1* | 4/2008 | DiMauro ............ | A61K 9/0009 424/400 |
| 2008/0208284 A1 | 8/2008 | Rezia et al. | |
| 2008/0294089 A1* | 11/2008 | Hardy ................. | A61K 9/0009 604/22 |
| 2008/0319376 A1 | 12/2008 | Wilcox et al. | |
| 2010/0035837 A1* | 2/2010 | Sasaki ................ | A61K 31/7016 514/53 |
| 2010/0081893 A1 | 4/2010 | Jarvik et al. | |
| 2011/0313328 A1 | 12/2011 | Nita | |
| 2011/0319927 A1 | 12/2011 | Nita | |
| 2012/0083717 A1 | 4/2012 | Alleman et al. | |
| 2012/0083718 A1 | 4/2012 | Alleman et al. | |

FOREIGN PATENT DOCUMENTS

| | | |
|---|---|---|
| JP | 05220152 A | 8/1993 |
| JP | 2003534032 A | 11/2003 |
| JP | 2004024668 A | 1/2004 |
| JP | 2012-509126 A | 4/2012 |
| WO | WO 2004/066856 A1 | 8/2004 |
| WO | WO 2005025403 A2 | 3/2005 |
| WO | WO-2012027722 A2 | 3/2012 |

OTHER PUBLICATIONS

Akiyama, Masahiko, et al., "Low-frequency Ultrasound Penetrates the Cranium and Enhances Thrombolysis In Vitro," *Neurosurgery: Technique Assessments*, vol. 43, Issue 4. Oct. 1998. (20 pgs).

Claassen, Jan, et al., "Effect of Cisternal and Ventricular Blood on Risk of Delayed Cerebral Ischemia After Subarachnoid Hemorrhage: The Fisher Scale Revisited," *Stroke: Journal of the American Heart Association*. Jun. 2001. (10 pgs).

Van Acker, Jos T., et al., "Automated Flow Cytometric Analysis of Cerebrospinal Fluid," *Clinical Chemistry*. 2001. (5 pgs).

Fujii, Yukihiko, et al., "Hemostatic Activation in Spontaneous Intracerebral Hemorrhage," *Stroke: Journal of the American Heart Association*. Jan. 2001. (9 pgs).

Kinouchi, Hiroyuki, et al., "Prevention of Symptomatic Vasospasm After Aneurysmal Subarachnoid Hemorrhage by Intraoperative Cisternal Figrinolysis Using Tissue-Type Plasminogen Activator Combined With Continuous Cisternal Drainage," *Neurol Med Chir (Tokyo)*. Jun. 2004. (9 pgs).

Newell, David W., et al., "Minimally invasive evacuation of spontaneous intracerebral hemorrhage using sonothrombolysis," *J Neurosurg*. Sep. 2011. (10 pgs).

Newell, David W., et al., "Sonothrombolysis is effective for minimally invasive evacuation of spontaneous intracerebral hemorrhage," *Fifth Annual Cerebrovascular Symposium*. Seattle, WA. May 2012. (46 pgs).

Stewart, Daphne, et al., "Distinct dose-dependent effects of plasmin and TPA on coagulation and hemorrhage," *Blood*. Apr. 2003. (5 pgs).

Washington, Chad W., et al., "Detection and Monitoring of Vasospasm and Delayed Cerebral Ischemia: A Review and Assessment of the Literature," *Neurocritical Care Society*. Jul. 2011. (6 pgs).

Lee, Benjamin, et al., "Operator Independent Transcranial Doppler Ultrasound for Continuous Monitoring of Cerebral Vessels," *Conference on Mathematics of Medical Imaging*. Toronto, Ontario, Canada. May 2012. (1 pg).

Extended European Search Report and Opinion dated Feb. 15, 2016 for Application No. 13805170.1, Applicant: David W. Newell, European Patent Office, 9 pages.

PCT International Search Report and Written Opinion for PCT/US2013/042744 filed May 24, 2013, Applicant: David W. Newell, dated Sep. 2, 2013, 14 pages.

Translated Notice of Rejection received from the Japan Patent Office for Japanese Patent Application No. 2015-517277, 5 pages.

* cited by examiner

TREATMENT OF SUBARACHNOID HEMATOMA USING SONOTHROMBOLYSIS AND ASSOCIATED DEVICES, SYSTEMS AND METHODS

CROSS-REFERENCE TO RELATED APPLICATION

This application claims the benefit of U.S. Provisional Patent Application No. 61/659,269, filed Jun. 13, 2012, which application is incorporated by reference herein in its entirety. To the extent the foregoing application and/or any other materials incorporated herein by reference conflict with the present disclosure, the present disclosure controls.

TECHNICAL FIELD

The present technology relates generally to neurological treatments. In particular, several embodiments are directed to using ultrasound energy to enhance hematoma resolution (e.g., to prevent cerebral vasospasm or to reduce the severity of cerebral vasospasm) in extravascular thrombolytic treatment regimes with relatively low probability of causing additional cerebral hemorrhage, e.g., due to the types and/or doses of thrombolytic agents used in the regimes.

BACKGROUND

Approximately 5,000,000 North Americans harbor intracranial aneurysms. The estimated annual rate of aneurysm rupture is about 10-28 per 100,000. Unfortunately, aneurysm ruptures are currently associated with relatively high morbidity and mortality. A large, international study reporting the results from surgical and medical management of patients admitted to neurosurgical services during a multiyear period in the early 1980s, revealed a mortality and morbidity rate of 42% among the North American patients. N. F. Kassell and J. C. Torner, *The International Cooperative Study on the Timing of Aneurysm Surgery—an Update*, 23 STROKE 205, 210 (1992). Therapeutic approaches to the treatment of subarachnoid hemorrhage have improved only modestly in the 40 years since this study. Among the many severe complications of subarachnoid hemorrhage, arterial narrowing resulting from cerebral vasospasm is perhaps the most pervasive and deleterious. This complication develops in about 40-70% of patients with aneurysmal subarachnoid hemorrhage and causes a delayed ischemic deficit in about 20-30% of those patients. It is generally considered to be the leading cause of mortality and morbidity in patients who have survived their initial hemorrhage.

A variety of treatments have been clinically tested for preventing cerebral vasospasm, reducing the severity of cerebral vasospasm, and/or reducing the ischemic effects of cerebral vasospasm. Tested therapeutic agents intended to prevent cerebral vasospasm or to reduce the severity of cerebral vasospasm include certain calcium channel blockers, endothelin receptor antagonists, and antispasmodics. These agents have mostly either failed to cause improved outcomes or provided only short lived effects. Nimodipine (a calcium channel blocker) and papaverine (an antispasmodic) have shown some promise, but still have little or no potential for robust prevention of cerebral vasospasm. Tested therapeutic agents intended to reduce the ischemic effects of cerebral vasospasm include certain N-methyl D-aspartate receptor antagonists and free radical scavengers. To date, these agents have also failed to significantly improve outcomes.

Since no single agent has been shown to be highly effective for improving outcomes following subarachnoid hemorrhage, standard treatments currently include a combination of therapies. The Triple-H therapy, which involves intravascularly administering a combination of drugs and fluid to induce hypervolemia, hypertension, and hemodilution, is currently the most widely used treatment. This approach is intended to increase blood flow through vasospastic vessels and thereby increase blood delivery to ischemic areas of the brain. Transluminal balloon angioplasty of major intracerebral arteries is also used in some cases with the same objective. Although useful, the Triple-H therapy and transluminal balloon angioplasty at best only partially reduce the ischemia associated with cerebral vasospasm. Their effect is often insufficient to prevent neurological impairment or even death. Furthermore, these approaches can have significant complications. For example, the Triple-H therapy can increase the rate of pulmonary edema, myocardial ischemia, hyponatremia, renal medullary washout, cerebral edema, and additional cerebral hemorrhage. Transluminal balloon angioplasty can increase the risk of surgically induced neurological damage, infection, and vessel stenosis.

Addressing cerebral vasospasm directly (e.g., preventing cerebral vasospasm or reducing the severity of cerebral vasospasm) has much greater potential for improving outcomes than merely mitigating the corresponding ischemic effects. Furthermore, since cerebral vasospasm typically has a delayed onset and a relatively gradual clinical course after hemorrhage (e.g., following aneurysm rupture), in most cases, there is a window of opportunity to apply preventative therapies. An effective approach for preventing cerebral vasospasm or reducing the severity of cerebral vasospasm has the potential annually to save thousands of lives and to prevent thousands of cases of neurological impairment. Accordingly, for this reason and/or for other reasons not stated herein, there is a need for innovation with respect to devices, systems, and methods for treating subarachnoid hematoma, cerebral vasospasm, and/or other related conditions.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Specific details of several embodiments of the present technology are described herein with reference to FIGS. 1-9. Although many of the embodiments are described herein with respect to devices, systems, and methods for treating subarachnoid hematoma using sonothrombolysis, other applications and other embodiments in addition to those described herein are within the scope of the present technology. For example, some embodiments may be useful for treating ischemic stroke and/or other neurological conditions. Additionally, several other embodiments of the present technology can have different configurations, components, or procedures than those described herein. A person having ordinary skill in the relevant art will understand that the present technology may have various additional embodiments, and that the present technology may be practiced without several of the details of the embodiments described herein with reference to FIGS. 1-9. The headings provided herein are for convenience only.

I. Cerebral Vasospasm

Figure 1:
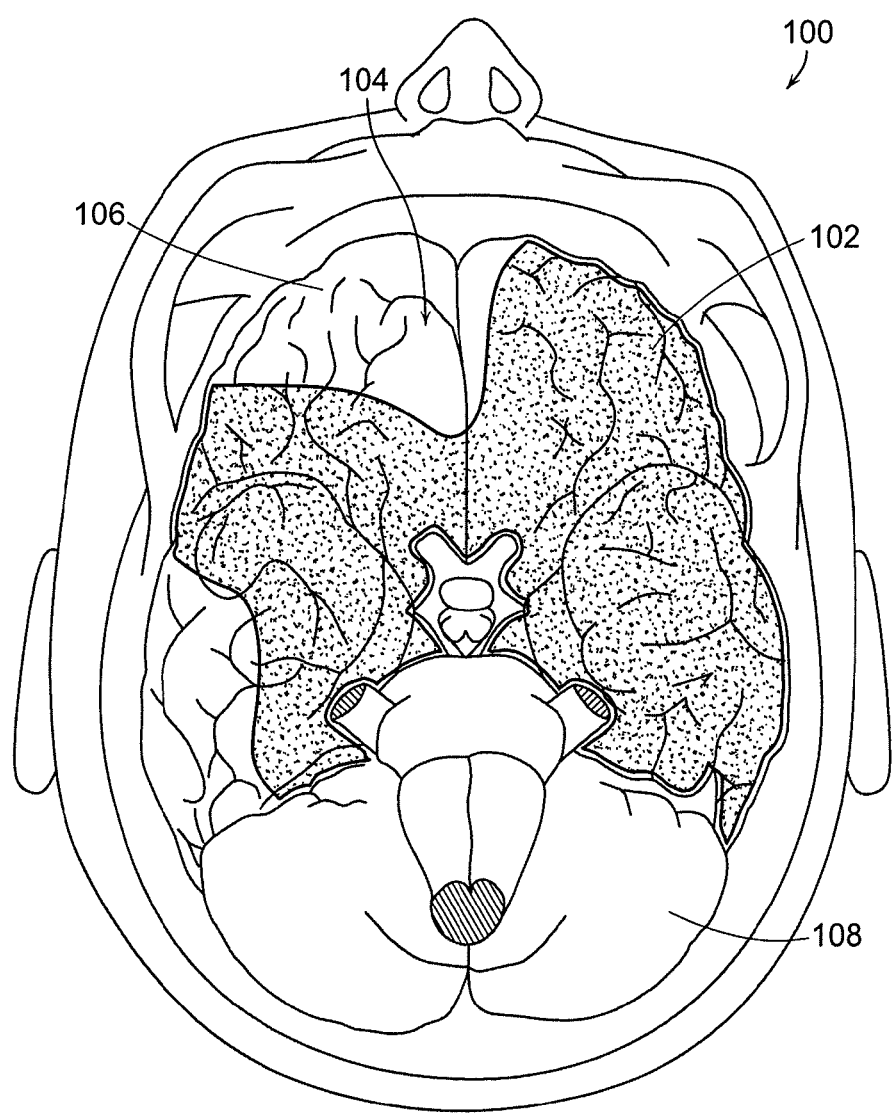
FIG. 1 is an inferior cranial view illustrating a patient having a subarachnoid hematoma.

Cerebral vasospasm includes blood vessel spasm and associated contraction of smooth muscle in the media of blood vessel walls. The condition is known to occur in the region of a subarachnoid hematoma. FIG. 1 is an inferior cranial view illustrating a patient 100 having a subarachnoid hematoma 102 at the basal cisterns 104 inferior to the temporal lobes 106 and anterior to the cerebellum 108. Several major cerebral and cerebellar arteries (not shown) are at or near the basal cisterns 104. These arteries are the primary blood supply for the brain. Accordingly, cerebral ischemia following spasm of these arteries triggered by the subarachnoid hematoma 102 can rapidly lead to neurological impairment or death. Although the basal cisterns 104 are a common location for blood to collect following intracerebral hemorrhage, other locations are also possible. Cerebral vasospasm of arteries at these other locations can also have serious complications.

Aneurysm rupture is the most common cause of subarachnoid hematoma leading to cerebral vasospasm, but other causes, such as trauma, tumor, or arteriovenous malformation, are also possible. Cerebral vasospasm does not occur in all cases of subarachnoid hematoma and, when it does occur, its onset is typically delayed. For example, it has been observed that cerebral vasospasm often occurs between the fourth and tenth day following aneurysmal subarachnoid hemorrhage. The clinical manifestation of cerebral vasospasm suggests that it may be associated with byproducts (e.g., vasoconstrictors or other vasoactive substances) of hematoma resolution. The underlying pathophysiological mechanism by which cerebral vasospasm leads to neurological ischemic deficit, however, is still poorly understood. Other proposed mechanisms include neuronal mechanisms, impairment of endothelial derived relaxant factors, proliferative vasculopathy, immunoreactive mechanisms, inflammatory mechanisms, mechanical phenomenon (e.g., stretching of arachnoid fibers or direct compression of vessels by the hematoma), and mechanisms associated with platelet aggregation, among others.

Although the exact pathophysiology of cerebral vasospasm may be unknown, evidence suggests that early removal of the associated hematoma is likely to prevent cerebral vasospasm or to at least reduce the severity of cerebral vasospasm. As discussed above, most subarachnoid hematomas occur in the basal cisterns. These hematomas may have various levels of coagulation and, in many cases, can be characterized as clots. Mechanically removing subarachnoid hematomas is usually not feasible without damaging nearby structures (e.g., basal cerebral arteries). Pharmacological approaches for removing subarachnoid hematomas, however, have great potential for preventing cerebral vasospasm or reducing the severity of cerebral vasospasm. There is also potential, however, for such approaches to cause side effects so severe as to offset their benefits. For example, although rapid resolution of subarachnoid hematomas is typically desirable, disruption of other intracranial blood clots can exacerbate cerebral hemorrhaging. In particular, disrupting blood clots around aneurysm ruptures or at the sites of surgical wounds (e.g., associated with surgical clipping or endovascular coiling) can cause additional hemorrhage into the subarachnoid space. There is also a possibility of additional cerebral hemorrhage from other locations as well as other serious side effects.

II. Sonothrombolysis

At least some embodiments of the present technology can include facilitating the removal (e.g., the complete or partial evacuation or other resolution) of subarachnoid hematomas with reduced side effects relative to conventional therapies. In some embodiments, a thrombolytic agent can be used in combination with therapeutic ultrasound energy. This combination, known generally as sonothrombolysis, has been shown to be effective in other applications. For example, sonothrombolysis has been shown to facilitate recanalization in the treatment of ischemic stroke. Solely by way of theory, the effect of ultrasound energy on the effect of thrombolytic agents is likely to be largely mechanical rather than chemical. For example, ultrasound energy may increase the binding of thrombolytic agents to binding sites within the structure of a hematoma by facilitating streaming and/or mixing of the thrombolytic agents into the structure. Other mechanisms are also possible.

Conventionally, using thrombolytic agents outside the vasculature has typically been discouraged or at least highly limited for neurological applications due to the possibility of causing or exacerbating cerebral hemorrhaging. Adding ultrasound energy to thrombolytic therapy, however, can facilitate the use of less aggressive thrombolytic agents and/or lower dosages of thrombolytic agents. For example, using ultrasound energy can allow the therapeutically effective treatment of subarachnoid hematoma with a type and/or dosage of a thrombolytic agent sufficiently low to cause only a minor or even a negligible or generally no increase in the clinical probability of causing or exacerbating additional cerebral hemorrhaging, e.g., rehemorrhaging from the origin of the hematoma. In some embodiments, a thrombolytic agent can be introduced at a dosage sufficiently low to cause less than a 10% increase in the clinical probability of rehemorrhage, such as less than a 5% increase or less than a 2% increase. Furthermore, the use of ultrasound energy in combination with a thrombolytic agent can facilitate the use of control algorithms for further limiting the dosage of the thrombolytic agent over time during a treatment regime so that it remains at or near a minimum therapeutically effective dosage.

III. Selected Examples

Figure 2:
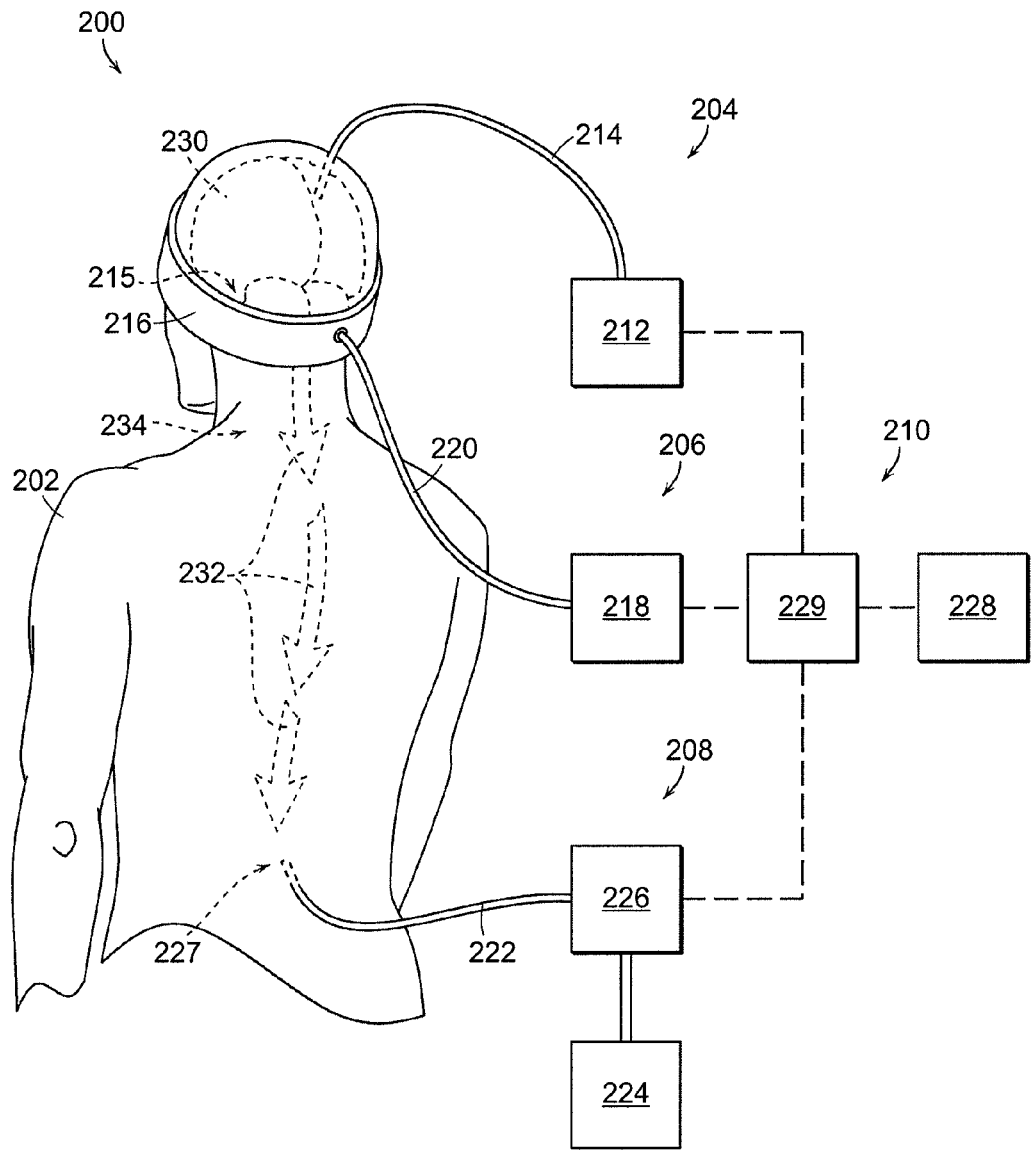
FIG. 2 is a partially schematic perspective view illustrating a therapeutic system during treatment of a patient having a subarachnoid hematoma in accordance with an embodiment of the present technology.

FIG. 2 is a partially schematic perspective view of a therapeutic system 200 during treatment of a patient 202 having a subarachnoid hematoma (not shown) in accordance with an embodiment of the present technology. The system 200 can include a thrombolytic delivery module 204, an ultrasound module 206, a drainage module 208, and a control module 210. The thrombolytic delivery module 204 can include a metering device 212 and a catheter 214 configured to deliver a thrombolytic agent into a subarachnoid region 215 of the patient 202, e.g., via a ventriculostomy. The ultrasound module 206 can include a headset 216, a power supply 218, and a power cord 220 extending between the headset 216 and the power supply 218. The headset 216 can be configured for hands-free delivery of transcranial ultrasound energy to the subarachnoid region 215. The drainage module 208 can include a drain line 222, a cerebrospinal fluid drain 224, and a cerebrospinal fluid analyzer 226 between the drain line 222 and the cerebrospinal fluid drain 224. The drain line 222 can be configured to drain cerebrospinal fluid including, without limitation, byproducts of hematoma resolution from a lumbar region 227 or another suitable region of the patient 202. The control module 210 can include a user interface 228 and a controller 229 operatively connected to the thrombolytic delivery module 204, the ultrasound module 206, and the drainage module 208. The thrombolytic delivery module 204 and the ultrasound module 206 can be included in a kit configured for treatment of subarachnoid hematoma. In some embodiments, the kit can further include the drainage module 208 and/or the control module 210.

In one example of a method in accordance with an embodiment of present technology, the patient 202 can first be diagnosed as having or likely having a subarachnoid hematoma. A ventriculostomy can then be performed and the catheter 214 can be inserted through the ventriculostomy into a ventricular space (not shown) of the patient's brain 230. The method can further include delivering a thrombolytic agent from the metering device 212 to cerebrospinal fluid within the ventricular space via the catheter 214. The metering device 212 can include a pump, a valve, a timer, a power source, a reservoir, and/or other suitable features. After being introduced, the thrombolytic agent can diffuse extravascularly within the cerebrospinal fluid and eventually migrate to the subarachnoid region 215 including the subarachnoid hematoma. In some cases, delivering the thrombolytic agent via a ventriculostomy can be useful to enhance contact between the thrombolytic agent and the subarachnoid hematoma and/or to facilitate flow of byproducts of hematoma resolution toward the drain line 222 along the path indicated by arrows 232. In other cases, the thrombolytic agent can be introduced intracisternally, intrathecally proximate the spinal cord, or in another suitable manner other than via a ventriculostomy.

The drainage module 208 can facilitate removing the byproducts of hematoma resolution. In some embodiments, cerebrospinal fluid including the byproducts can be slowly drained from the patient 202 via the drain line 222 while delivering ultrasound energy to the subarachnoid region 215 using the headset 216. Although the drain line 222 shown in FIG. 2 is connected to the lumbar region 227, other suitable locations for draining cerebrospinal fluid can also be used. For example, the drain line 222 can be intrathecally connected to the patient 202 at a cervical region 234 closer to the subarachnoid region 215 than the lumbar region 227. Furthermore, in some embodiments, the thrombolytic delivery module 204 and the ultrasound module 206 can be used without the drainage module 208. For example, in some cases, merely dispersing the byproducts of hematoma resolution through the cerebrospinal fluid can be sufficient to prevent cerebral vasospasm or to reduce the severity of cerebral vasospasm.

Before or after beginning delivery of the thrombolytic agent, the headset 216 can be connected to the patient 202. The headset 216 can include one or more ultrasound transducers (not shown) and can be fitted to the patient 202 such that the transducers are positioned to direct therapeutic ultrasound energy to the subarachnoid region 215. For example, the headset 216 can be configured for hands-free delivery of transcranial ultrasound energy to the subarachnoid region 215. In some cases, treatment regimes in accordance with embodiments of the present technology can extend over many hours or days. In these and other cases, hands-free delivery of transcranial ultrasound energy can be more practical and/or reliable than delivery of ultrasound energy using techniques that involve the continuous presence of a clinician. Connecting the headset 216 to the patient 202 can include applying an ultrasound gel to the patient 202 and then fitting the headset 216 snuggly so that it generally remains in position during the treatment. In some embodiments, the headset 216 can be adjustable to conform to a variety of head sizes. The positioning of the headset 216 can be periodically monitored during the treatment to determine if shifting has occurred. After positioning, the headset 216 can be activated to deliver ultrasound energy to the subarachnoid region 215 so as to enhance the thrombolytic effect of the thrombolytic agent. Enhancing the thrombolytic effect of the thrombolytic agent can include, for example, increasing the rate of hematoma resolution by at least about 20%, at least about 50%, or at least about 100%. Although the headset 216 is shown in FIG. 2 as a band, in other embodiments the headset 216 can have other suitable forms. For example, the headset 216 can be a helmet or can have a form that is not fully circumferential. Additional details regarding the headset 216 are described below with reference to FIGS. 3-6.

The control module 210 can be configured to automatically or manually control operation of all or a portion of the system 200. In some embodiments, the controller 229 can be programmed to receive input from the ultrasound module 206 and/or the drainage module 208 and to control operation of one or more aspects of the system 200 in accordance with the input. For example, the controller 229 can be programmed to receive a signal from the ultrasound module 206 and to control delivery of a thrombolytic agent from the metering device 212 to the subarachnoid region 215 in response to the signal, to control delivery of ultrasound energy from the headset 216 to the subarachnoid region 215 in response to the signal, or both. Furthermore, the controller 229 can be programmed to receive a signal from the drainage module 208 and to control delivery of a thrombolytic agent from the metering device 212 to the subarachnoid region 215 in response to the signal, to control delivery of ultrasound energy from the headset 216 to the subarachnoid region 215 in response to the signal, or both. Controlling delivery of the thrombolytic agent can include, for example, controlling continuous or intermittent administration (e.g., the rate of administration) of the thrombolytic agent over time. Controlling delivery of the ultrasound energy can include, for example, controlling the frequency, intensity, duty cycle, waveform, pulse pattern, and/or other suitable parameters of the ultrasound energy over time.

The ultrasound module 206 and/or the drainage module 208 can have diagnostic functionality for generating information that can be used by the controller 229 and/or displayed by the user interface 228. For example, the headset 216 can be configured to ultrasonically detect blood-flow velocity in one or more arteries (e.g., the middle cerebral artery or an intracranial portion of the internal carotid artery) proximate (e.g., at or near) the subarachnoid hematoma and to transmit a corresponding signal to the controller 229. In such embodiments, the headset 216 can include one or more transducers configured to receive ultrasound echoes that can be processed based on the Doppler effect to determine the blood-flow velocity. Blood-flow velocity can be a reliable indicator of the likely clinical course of cerebral vasospasm in the patient 202. For example, the trajectory of increasing blood-flow velocity can indicate the likely peak severity of the cerebral vasospasm. Accordingly, when the ultrasound module 206 detects a rapid increase in blood-flow velocity, the controller 229 can be programmed to cause a higher dosage of the thrombolytic agent to be introduced into the subarachnoid region 215, and when the ultrasound module 206 detects a slow increase in blood-flow velocity, the controller 229 can be programmed to cause a lower dosage of the thrombolytic agent to be introduced into the subarachnoid region 215. Details of diagnostic functionality and other potentially useful aspects of the headset 216 are described in detail in U.S. Pat. No. 6,733,450, which is incorporated by reference herein in its entirety.

The drainage module 208 can be configured to detect one or more indicators of resolution of the subarachnoid hematoma and to transmit a corresponding signal to the controller 229. Such indicators can include, for example, concentrations of byproducts of hematoma resolution (e.g., red blood cells) or other chemical markers within the cerebrospinal fluid corresponding to hematoma resolution. In some embodiments, the cerebrospinal fluid analyzer 226 is a flow cytometer configured to detect these concentrations continuously or intermittently over time. Information from the cerebrospinal fluid analyzer 226 can indicate the rate of hematoma resolution. Accordingly, when the drainage module 208 detects rapid resolution of the subarachnoid hematoma, the controller 229 can be programmed to cause a lower dosage of the thrombolytic agent to be introduced into the subarachnoid region 215, and when the drainage module 208 detects slow resolution of the subarachnoid hematoma, the controller 229 can be programmed to cause a higher dosage of the thrombolytic agent to be introduced into the subarachnoid region 215. Similarly, when the drainage module 208 detects slow resolution of the subarachnoid hematoma, the controller 229 can be programmed to cause the ultrasound energy to be introduced into the subarachnoid region 215 at a different intensity, frequency, and/or other suitable parameter. The parameters of the ultrasound energy can be varied, for example, until the rate of resolution of the subarachnoid hematoma increases to a sufficient level.

The diagnostic functionality of the ultrasound module 206 and the drainage module 208 can be eliminated in some embodiments. In addition to or instead of controlling the system 200 in response to input from the ultrasound module 206 and/or the drainage module 208, the controller 229 can be programmed to control operation of the system 200 according to predetermined treatment parameters, such as parameters of predetermined treatment regimes including dosages of the thrombolytic agent, frequencies of the ultrasound energy, intensities of the ultrasound energy, and/or other suitable parameters over time. The controller 229 can be programmed to receive these parameters directly from the user interface 228 and/or to calculate these parameters based on other data from the user interface 228. A user may input patient information (e.g., age, sex, weight, etc.) and condition information (e.g., elapsed time since aneurysmal rupture, approximate hematoma volume, etc.) and the controller 229 can use this information to determine parameters of the treatment based on programmed algorithms. For example, when the elapsed time since aneurysmal rupture is relatively long (e.g., greater than about 36 hours) and/or the approximate hematoma volume is relatively high (e.g., greater than about 15 mL), a more aggressive treatment regime can be used. Similarly, when the elapsed time since aneurysmal rupture is relatively short (e.g., less than about 24 hours) and/or the approximate hematoma volume is relatively low (e.g., less than about 10 mL), a less aggressive treatment regime can be used. Many suitable variations of the control module 210 are possible. Furthermore, in some embodiments, the control module 210 can be eliminated and the thrombolytic delivery module 204, the ultrasound module 206, and/or the drainage module 208 can be operated independently under the supervision of one or more clinicians.

Figure 3:
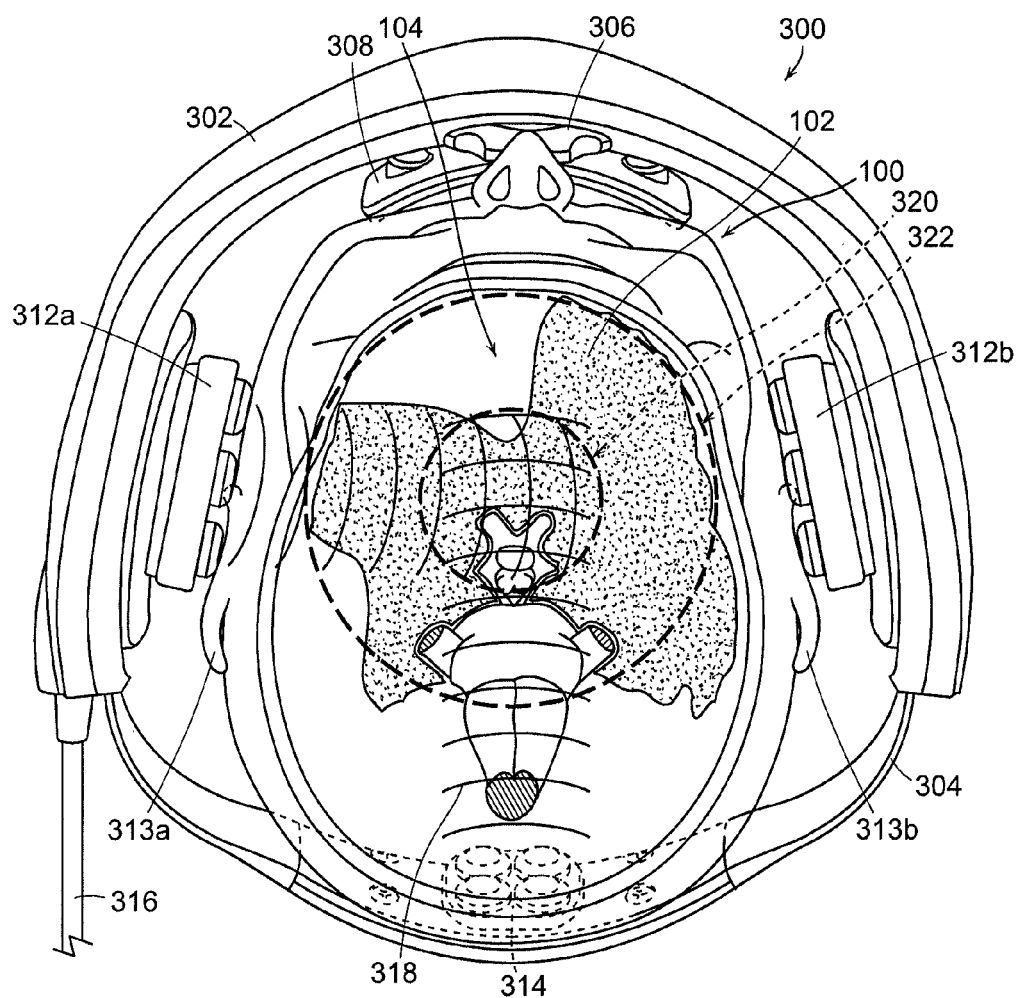
FIG. 3 is an inferior cranial view of the patient shown in FIG. 1 during sonothrombolysis using a commercially available headset in accordance with an embodiment of the present technology.

In some embodiments, the headset 216 shown in FIG. 2 can be a commercially available headset, such as a commercially available headset indicated for the treatment of ischemic stroke in the basal cerebral arteries. One example of such a headset is the CLOTBUST ER available from Cerevast Therapeutics, Inc. (Redmond, Wash.). FIG. 3 is an inferior cranial view of the patient 100 shown in FIG. 1 during sonothrombolysis using a commercially available headset 300 in accordance with an embodiment of the present technology. The temporal lobes 106 and the cerebellum 108 are not shown to facilitate illustration. As shown in FIG. 3, the headset 300 can include an anterior headframe member 302, a posterior headframe member 304, and a knob 306 that can be turned to draw portions of the posterior headframe member 304 into the anterior headframe member 302 and thereby tighten the headset 300 around the patient's head. The anterior headframe member 302 can be configured to contact the patient 100 at the brow, and the posterior headframe member 304 can be configured to contact the patient 100 at the back of the neck. The headset 300 can further include an anterior brace 308 that can facilitate positioning the headset 300. As shown in FIG. 3, the headset 300 can include lateral transducer assemblies 312a, 312b proximate the patient's ears 313a, 313b, and a posterior transducer assembly 314 centered on the anterior headframe member 302. Power and control signals for the transducer assemblies 312a, 312b, 314 can be conveyed to the headset 300 via a cable 316. The headset 300 can be configured to operate the transducer assemblies 312a, 312b, 314 according to a variety of suitable patterns (e.g., patterns of frequency, intensity, duty cycle, wave form, or other suitable parameters). Details of these patterns and other potentially useful aspects of the headset 300 are described in detail in U.S. Patent Application Publication Nos. 2012/0083717 and 2012/0083718, which are incorporated by reference herein in their entireties. Ultrasound energy 318 is shown in FIG. 3 emanating from only the transducer assemblies 312a, 314 and from the groups of transducers rather than from the individual transducers to facilitate illustration.

With reference to FIG. 3, the headset 300 can be configured to deliver the ultrasound energy 318 to the basal cisterns 104 while reducing exposure of the parenchyma of the brain (e.g., including the temporal lobes 106) to the ultrasound energy 318. This can be useful, for example, to reduce the level of sonothrombolysis outside the basal cisterns 104. When the subarachnoid hematoma 102 is the result of an intracerebral hemorrhage, the ultrasound energy 318 can be directed toward the basal cisterns 104 such that an intensity of the ultrasound energy at the basal cisterns 104 is greater (e.g., at least 50% greater or at least 100% greater) than an intensity of the ultrasound energy at an origin of the intracerebral hemorrhage. This can be useful in some cases to reduce the possibility of causing additional hemorrhage at the origin of the intracerebral hemorrhage. Furthermore, while long-duration exposure to low-intensity ultrasound is generally considered to be safe for brain tissue, reducing such exposure can still be desirable to reduce the possibility of unknown side effects, particularly in cases in which the exposure is not therapeutically useful.

The headset 300 can be configured for alignment with craniological landmarks so that the transducer assemblies 312a, 312b, 314 direct the ultrasound energy 318 into a central region 320 of the basal cisterns 104. The major cerebral and cerebellar arteries are primarily located in the central region 320, making it a relevant treatment region for ischemic stroke. Delivering the ultrasound energy 318 into the central region 320 can also be useful for sonothrombolysis of subarachnoid hematomas. As shown in FIG. 3, however, the subarachnoid hematoma 102 can also extend into a peripheral region 322 of the basal cisterns 104. Sonothrombolysis of the subarachnoid hematoma 102 at both the central region 320 and the peripheral region 322 can increase the rate of resolution. In some cases, it can be more difficult for a thrombolytic agent to access portions of the subarachnoid hematoma 102 at the central region 320 than portions of the subarachnoid hematoma 102 at the peripheral region 322. The potential for sonothrombolysis, therefore, may be greater at the peripheral region 322 than at the central region 320. The exact positions of subarachnoid hematomas vary from patient to patient and may change over the course of therapy as the subarachnoid hematomas shrink. Accordingly, in some embodiments, the ultrasound energy 318 can be delivered (e.g., generally evenly delivered) over a broader portion (e.g., generally all) of the basal cisterns 104 (or even to more distant subarachnoid regions) than would typically be contemplated for the treatment of ischemic stroke.

Figure 4:
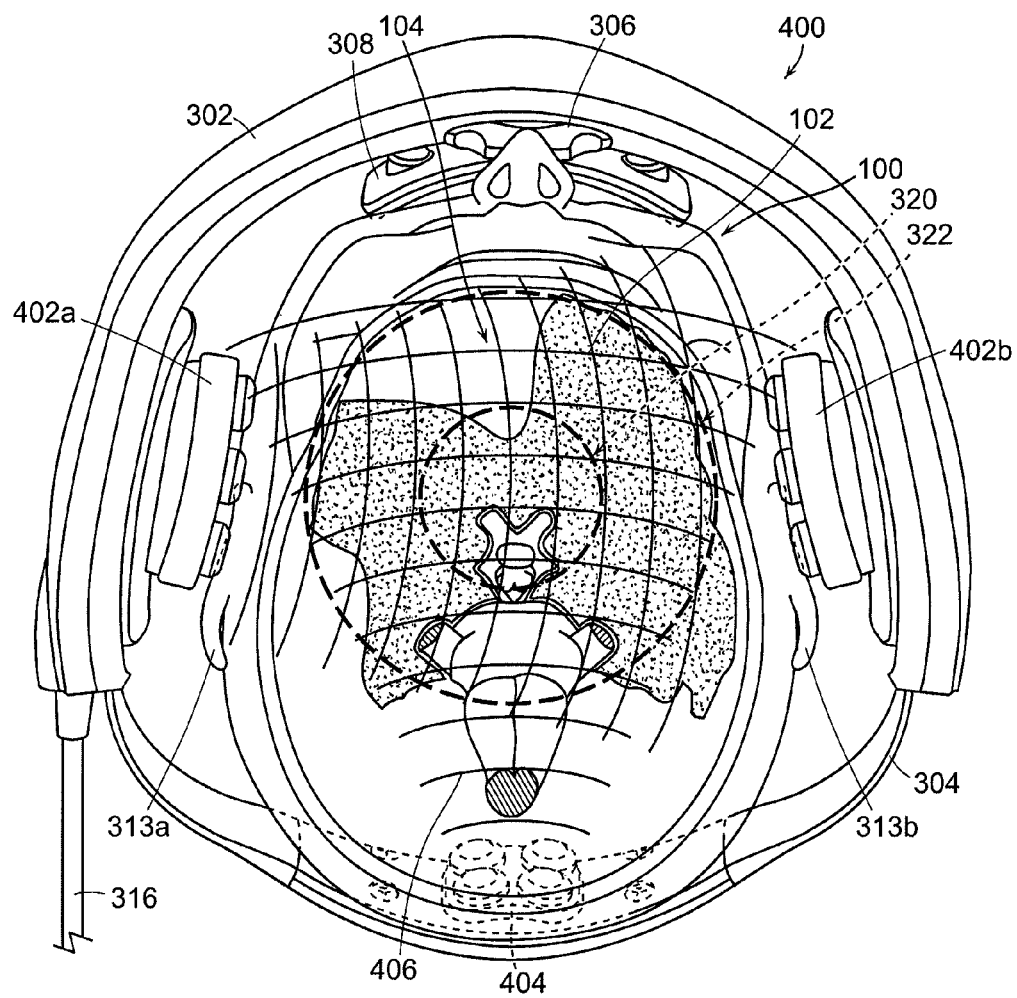
FIGS. 4-6 are inferior cranial views of the patient shown in FIG. 1 during sonothrombolysis using other headsets in accordance with embodiments of the present technology.
Figure 5:
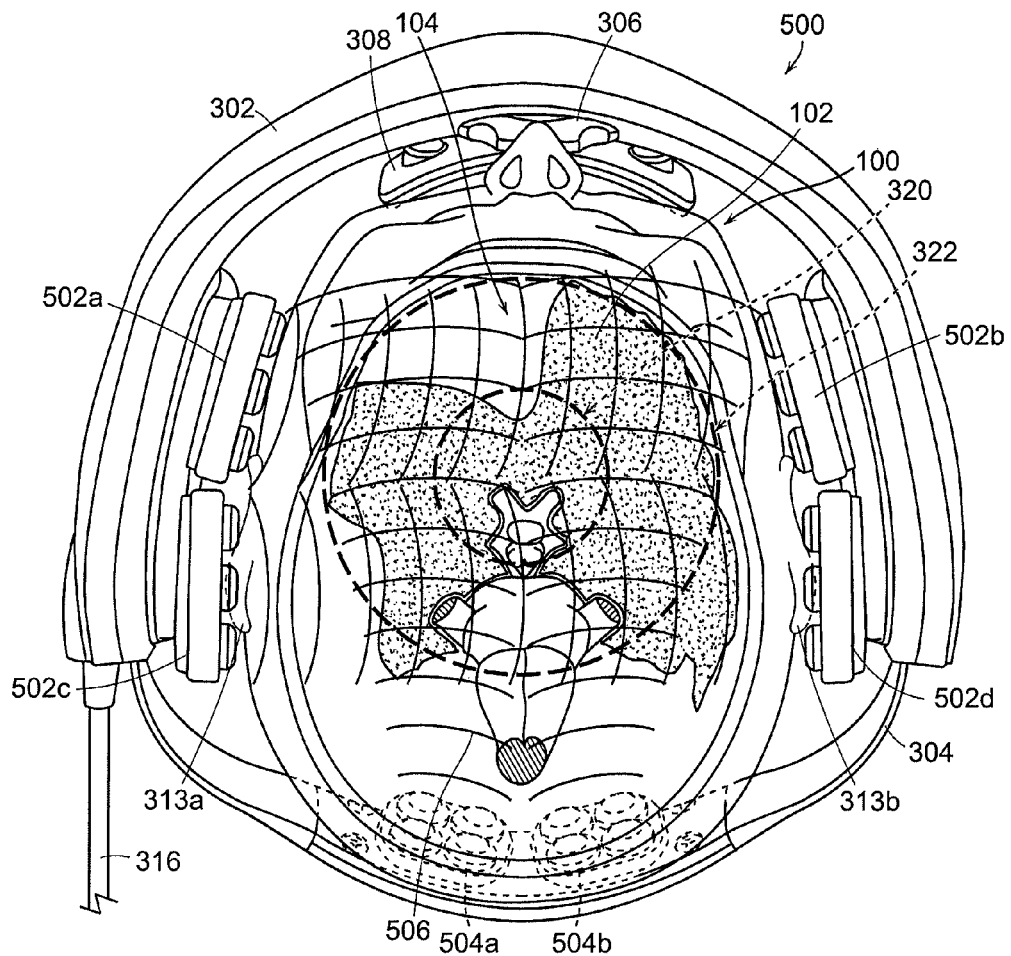
Figure 6:
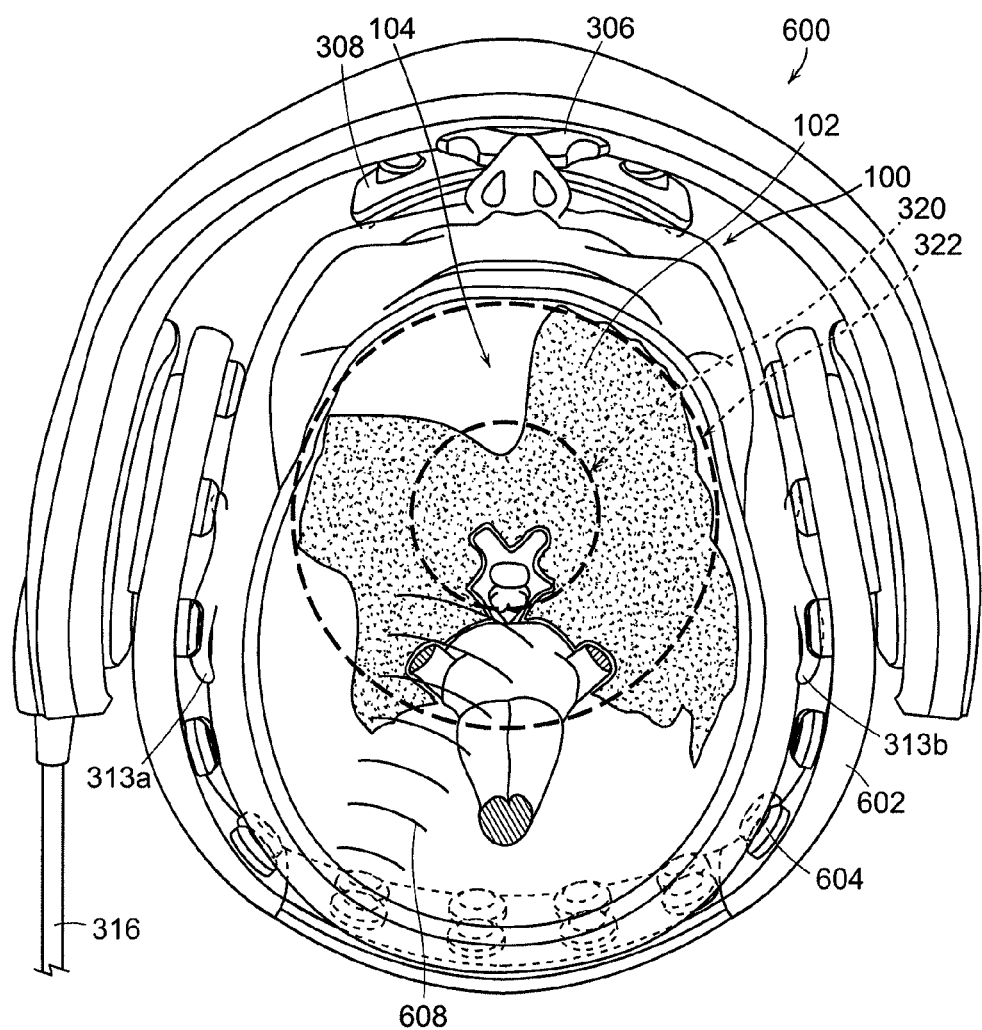

FIGS. 4-6 are inferior cranial views of the patient 100 shown in FIG. 1 during sonothrombolysis using other headsets in accordance with embodiments of the present technology. As in FIG. 3, the temporal lobes 106 and the cerebellum 108 are not shown and the depiction of ultrasound energy is simplified in FIGS. 4-6 to facilitate illustration. As shown in FIG. 4, a headset 400 configured in accordance with a particular embodiment can include lateral transducer assemblies 402a, 402b and a posterior transducer assembly 404 having convex shapes configured to broaden delivery of ultrasound energy 406 to the peripheral region 322. In other embodiments, the shape characteristics of piezoelectric crystals (not shown) of individual transducers of the transducer assemblies 402a, 402b, 404 can selected to broaden delivery of the ultrasound energy 406 with or without the transducer assemblies 402a, 402b, 404 being convex. As shown in FIG. 5, another headset 500 can include four lateral transducer assemblies 502a-d and two posterior transducer assemblies 504a, 504b positioned to deliver ultrasound energy 506 to both the central region 320 and the peripheral region 322 of the basal cisterns 104. In other embodiments, the headset 500 can have other suitable numbers and arrangements of transducer assemblies. As shown in FIG. 6, another headset 600 can include a curved transducer assembly 602 configured to extend generally continuously between temporal regions 604a, 604b of the patient 100. The curved transducer assembly 602 can include a plurality of individual transducers 606 (one labeled in FIG. 6) distributed along its length. In some embodiments, the curved transducer assembly 602 can be at least partially flexible and/or adjustable to better conform to patients of different sizes. The headset 600 can be well suited for delivering ultrasound energy 608 generally evenly though at least the posterior half of the peripheral region 322.

Figure 7:
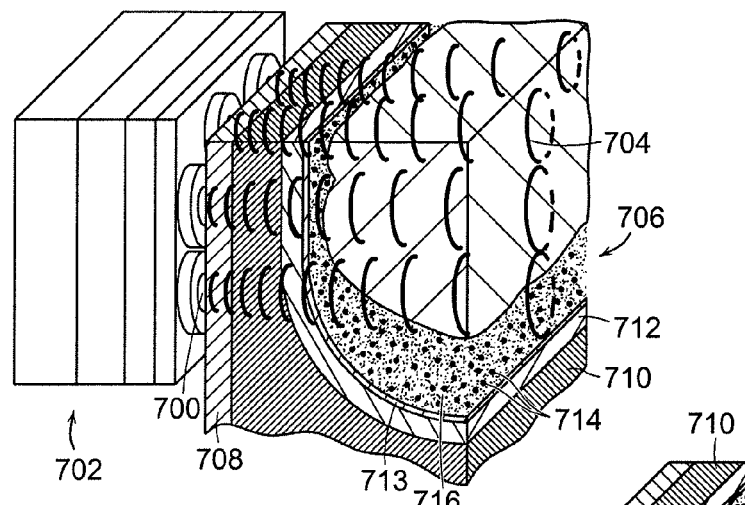
FIG. 7 is a partially schematic cross-sectional view illustrating delivery of ultrasound energy into a subarachnoid region in accordance with an embodiment of the present technology.
Figure 8:
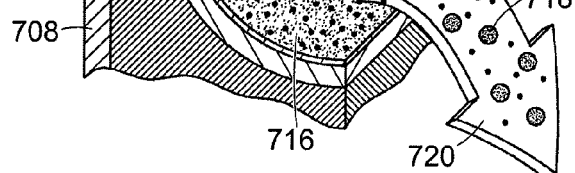
FIG. 8 is a partially schematic cross-sectional view illustrating resolution of a subarachnoid hematoma in accordance with an embodiment of the present technology.
Figure 9:
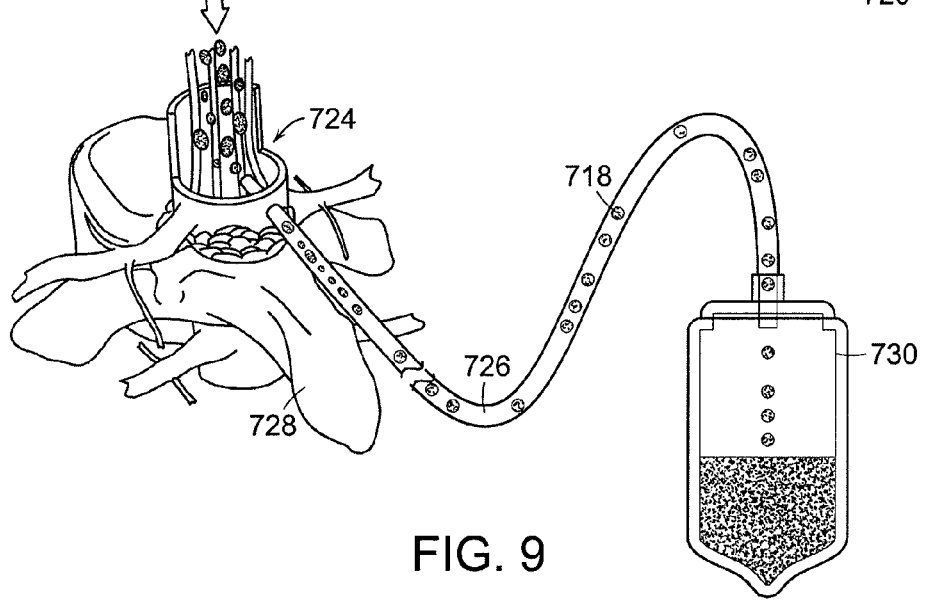
FIG. 9 is a partially schematic perspective view illustrating drainage of cerebrospinal fluid in accordance with an embodiment of the present technology.

FIGS. 7-8 are partially schematic cross-sectional views and FIG. 9 is a partially schematic perspective view illustrating aspects of sonothrombolysis in accordance with an embodiment of the present technology. As shown in FIG. 7, a plurality of transducers 700 in a transducer assembly 702 can deliver ultrasound energy 704 transcranially to a subarachnoid space 706. The ultrasound energy 704 can travel through several anatomical layers including the skin 708, the skull 710, the dura mater 712, and the arachnoid 713. As discussed above with reference to FIG. 2, frequency, intensity, duty cycle, waveform, pulse pattern, and/or other suitable parameters of the ultrasound energy 704 can be selected manually or automatically (e.g., based on clinical factors). For example, reducing the possibility of undesirable side effects (e.g., additional cerebral hemorrhaging) and increasing the rate of hematoma resolution are often competing objectives that can be considered case-by-case before initiating a treatment regime and reconsidered intermittently or continuously during a treatment regime to inform the selection of appropriate parameters for the ultrasound energy 704. In some cases, using lower intensities and/or higher frequencies can reduce the probability of undesirable side effects while using higher intensities and/or lower frequencies can increase the rate of hematoma resolution. Various different or additional effects and correlations are also possible.

Ultrasound at lower frequencies typically penetrates more effectively through anatomical layers (e.g., the skin 708, the skull 710, the dura mater 712, and the arachnoid 713 shown in FIGS. 7-8) than ultrasound at higher frequencies. Ultrasound at lower frequencies, however, can also be more disruptive and potentially damaging to small cerebral blood vessels than ultrasound at higher frequencies. In some embodiments, the frequency of the ultrasound energy 704 can be selected to be relatively high (e.g., greater than about 3 MHz, greater than about 3.5 MHz, or greater than about 4 MHz). This can cause sonothrombolysis to occur primarily in the peripheral region 322 (FIGS. 3-6) and reduce potential side effects of using lower frequencies and/or delivering the ultrasound energy 704 to the central region 320 (FIGS. 3-6). In other embodiments, using lower frequencies may be appropriate. Suitable frequencies for the ultrasound energy 704 can include, for example, frequencies between about 0.5 and about 5 MHz, between about 1 and about 4 MHz, or within other suitable ranges. Suitable intensities for the ultrasound energy 704 can include, for example, intensities less than about 5 W/cm$^2$, less than about 3.5 W/cm$^2$, less than about 2 W/cm$^2$, between about 0.1 and about 5 W/cm$^2$, between about 0.2 and about 3.5 W/cm$^2$, or within other suitable ranges.

Within the subarachnoid space 706, the ultrasound energy 704 can facilitate mixing between a thrombolytic agent 714 and coagulated blood 716 or otherwise enhance activity of the thrombolytic agent 714. For simplicity of illustration, the thrombolytic agent 714 and the coagulated blood 716 are shown schematically in FIG. 7 distributed generally evenly throughout the subarachnoid space 706. More typically, different portions of the subarachnoid space 706 may have different concentrations of the thrombolytic agent 714 and the coagulated blood 716. For example, central portions of the subarachnoid space 706 within the basal cisterns may have lower concentrations of the thrombolytic agent 714 and greater concentrations of the coagulated blood 716 than peripheral portions of the subarachnoid space 706. As shown in FIGS. 8-9, the thrombolytic agent 714 and resolution products 718 can migrate in the direction of arrows 720, 722 down the spinal canal 724 to a drain line 726 proximate a lumbar vertebra 728. From the drain line 726, the thrombolytic agent 714 and resolution products 718 can be collected in a collection bag 730.

Although many embodiments of the present technology are described herein with respect to the use of ultrasound energy to cause an enhanced thrombolytic effect, other suitable forms of energy can also be used. For example, the ultrasound module 206 shown in FIG. 2 can be an energy delivery module configured to deliver thermal energy, electromagnetic (e.g., radiofrequency) energy, or another suitable type of mechanical energy (e.g., vibration or acoustic streaming).

Suitable thrombolytic agents 714 can include, for example, tissue plasminogen activators (e.g., alteplase, retaplase, and tenecteplase), streptokinase, anistreplase, and urokinase among others. The type and/or dosage of the thrombolytic agent 714 can be selected based on the enhanced thrombolytic effect associated with use of the ultrasound energy 704. Therapeutically effective dosages can vary according to factors such as the type of the thrombolytic agent 714, the physical characteristics of the patient, and the severity of the condition. In a particular example of suitable treatment regime, a tissue plasminogen activator can be administered via a ventriculostomy at a dosage of about 1 mg every 8 hours, with transcranial ultrasound applied for about 2 hours following each administration. In some embodiments, the thrombolytic agent 714 can include a combination of multiple drugs or other agents (e.g., anticoagulants). Furthermore, a sonothrombolysis enhancing agent can be introduced extravascularly into the subarachnoid space 706 along with or separate from the thrombolytic agent 714. The sonothrombolysis enhancing agent can include, for example, echogenic microbubbles or other contrast-enhancing agents commercially available for use in diagnostic ultrasonography. Such particles are typically buoyant, which is of little or no consequence during intravascular use. In some embodiments of the present technology, however, sonothrombolysis enhancing particles can be selected to be generally non-buoyant so that, after they are introduced (e.g., via a ventriculostomy), they can sink within the cerebrospinal fluid and settle by gravity into the basal cisterns. This can be useful, for example, to enhance the selectivity of sonothrombolysis to an area including a subarachnoid hematoma with reduced possibility of sonothrombolysis within intraparenchymal portions of the brain and the associated possibility of additional intracerebral hemorrhaging.

Sonothrombolysis in accordance with the present technology has significant potential for preventing cerebral vasospasm or reducing the severity of cerebral vasospasm or other complications of subarachnoid hematoma in patients. Analytical measures of cerebral vasospasm include, for example, blood-flow velocities in arteries (e.g., the middle cerebral artery and intracranial portions of the internal carotid artery) proximate the subarachnoid hematoma. Another useful measure can be the ratio of blood-flow velocity in the middle cerebral artery to blood-flow velocity in an extracranial portion of the internal carotid artery. In some embodiments, sonothrombolysis in accordance with the present technology can maintain blood-flow velocity in generally all arteries proximate a subarachnoid hematoma at less than about 120 cm/sec (e.g., less than about 160 or about 200 cm/sec) for at least about 14 days after first administering a thrombolytic agent. In these and other embodiments, a ratio of blood-flow velocity in the middle cerebral artery to blood-flow velocity in an extracranial portion of the internal carotid artery can be generally maintained at less than about 3 (e.g., less than about 4 or about 6) for at least about 14 days after first administering a thrombolytic agent. It is expected that embodiments of the present technology may achieve these and other results at a statistically significant greater rate of occurrence relative to control.

IV. Conclusion

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while stages may be presented in a given order, alternative embodiments may perform stages in a different order. The various embodiments described herein and elements thereof may also be combined to provide further embodiments. In some cases, well-known structures and functions have not been shown or described in detail to avoid unnecessarily obscuring the description of embodiments of the present technology.

Certain aspects of the present technology may take the form of computer-executable instructions, including routines executed by a controller or other data processor. In some embodiments, a controller or other data processor configured in accordance with the present technology can be specifically programmed, configured, or constructed to perform one or more of these computer-executable instructions. Furthermore, some aspects of the present technology may take the form of data stored or distributed on computer-readable media, including magnetic or optically readable or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Where the context permits, singular or plural terms may also include the plural or singular terms, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout the disclosure to mean including at least the recited feature(s) such that any greater number of the same feature(s) and/or additional types of other features are not precluded. It will also be appreciated that various modifications may be made to the described embodiments without deviating from the present technology. Further, while advantages associated with certain embodiments of the present technology may have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

I claim:

1. A method of treating a human patient having a basal subarachnoid region and a basal subarachnoid hematoma at the basal subarachnoid region, the method comprising:
   introducing a thrombolytic agent extravascularly into the basal subarachnoid region;
   connecting a headset to the patient, wherein the headset comprises ultrasound transducers and is configured for hands-free delivery of ultrasound energy through the patient's skull to the basal subarachnoid region; and
   delivering ultrasound energy from the headset through the patient's skull to the basal subarachnoid region to enhance a thrombolytic effect of the thrombolytic agent.

2. The method of claim 1, wherein delivering the ultrasound energy to the basal subarachnoid region includes delivering the ultrasound energy throughout the patient's basal cisterns.

3. The method of claim 1, wherein delivering the ultrasound energy includes delivering the ultrasound energy at a frequency greater than 3.5 MHz.

4. The method of claim 1, wherein introducing the thrombolytic agent includes introducing the thrombolytic agent at a dosage sufficiently low to cause less than a 5% increase in a clinical probability of rehemorrhage.

5. The method of claim 1, further comprising selecting a dosage of the thrombolytic agent based on the enhanced thrombolytic effect.

6. The method of claim 1, further comprising selecting a type of the thrombolytic agent based on the enhanced thrombolytic effect.

7. The method of claim 1, wherein:
   the basal subarachnoid hematoma is the result of an intracerebral hemorrhage; and
   delivering the ultrasound energy includes directing the ultrasound energy toward the basal subarachnoid region such that an intensity of the ultrasound energy at the basal subarachnoid region is greater than an intensity of the ultrasound energy at an origin of the intracerebral hemorrhage.

8. The method of claim 1, wherein introducing the thrombolytic agent includes introducing the thrombolytic agent via a ventriculostomy.

9. The method of claim 1, wherein introducing the thrombolytic agent includes introducing the thrombolytic agent intracisternally.

10. The method of claim 1, wherein introducing the thrombolytic agent includes introducing the thrombolytic agent intrathecally proximate the patient's spinal cord.

11. The method of claim 1, further comprising draining cerebrospinal fluid from the patient.

12. The method of claim 11, wherein draining the cerebrospinal fluid from the patient includes draining the cerebrospinal fluid from the patient while delivering the ultrasound energy to the basal subarachnoid region.

13. The method of claim 1, further comprising ultrasonically monitoring blood-flow velocity using the headset.

14. The method of claim 13, further comprising controlling a dosage of the thrombolytic agent in response to the blood-flow velocity.

15. The method of claim 1, further comprising introducing a sonothrombolysis enhancing agent extravascularly into the basal subarachnoid region.

16. The method of claim 15, wherein:
   the sonothrombolysis enhancing agent includes non-buoyant particles; and
   introducing the sonothrombolysis enhancing agent includes introducing the sonothrombolysis enhancing agent via a ventriculostomy.

17. The method of claim 1, further comprising preventing cerebral vasospasm or reducing a severity of cerebral vasospasm in the patient.

18. The method of claim 17, wherein preventing cerebral vasospasm or reducing the severity of cerebral vasospasm in the patient includes:
   maintaining blood-flow velocity in the patient's middle cerebral artery and intracranial portions of the patient's internal carotid artery at less than 200 cm/sec for at least 14 days after introducing the thrombolytic agent; and
   maintaining a ratio of blood-flow velocity in the middle cerebral artery to blood-flow velocity in an extracranial portion of the internal carotid artery at less than 6.

19. The method of claim 17, wherein preventing cerebral vasospasm or reducing the severity of cerebral vasospasm in the patient includes maintaining blood-flow velocity in all of the patient's arteries proximate the basal subarachnoid hematoma at less than 120 cm/sec for at least 14 days after introducing the thrombolytic agent.

20. The method of claim 17, wherein preventing cerebral vasospasm or reducing the severity of cerebral vasospasm in the patient includes maintaining blood-flow velocity in all of the patient's arteries proximate the basal subarachnoid hematoma at less than 200 cm/sec for at least 14 days after introducing the thrombolytic agent.

21. The method of claim 17, wherein preventing cerebral vasospasm or reducing the severity of cerebral vasospasm in the patient includes:
   maintaining blood-flow velocity in the patient's middle cerebral artery and intracranial portions of the patient's internal carotid artery at less than 120 cm/sec for at least 14 days after introducing the thrombolytic agent; and
   maintaining a ratio of blood-flow velocity in the middle cerebral artery to blood-flow velocity in an extracranial portion of the internal carotid artery at less than 3.

* * * * *